(12) United States Patent
Osora et al.

(10) Patent No.: US 6,812,260 B2
(45) Date of Patent: Nov. 2, 2004

(54) METHOD OF CONDUCTING AN EXOTHERMIC REACTION

(75) Inventors: Hiroyuki Osora, Hiroshima (JP); Yoshio Seiki, Hiroshima (JP); Tetsuya Imai, Hiroshima (JP); Kazuto Kobayashi, Hiroshima (JP); Chie Kuwada, Hiroshima (JP); Kazuhiro Morita, Tokyo (JP); Shuichi Miyamoto, Tokyo (JP)

(73) Assignees: Mitsubishi Heavy Industries, Ltd., Tokyo (JP); Mitsubishi Gas Chemical Company, Inc., Tokyo (JP)

( * ) Notice: Subject to any disclaimer, the term of this patent is extended or adjusted under 35 U.S.C. 154(b) by 68 days.

(21) Appl. No.: 10/241,457

(22) Filed: Sep. 12, 2002

(65) Prior Publication Data

US 2003/0047851 A1 Mar. 13, 2003

(30) Foreign Application Priority Data

Sep. 13, 2001 (JP) ........................................ 2001-278243

(51) Int. Cl.[7] .............................................. C07C 27/00
(52) U.S. Cl. ........................ 518/713; 518/700; 518/717
(58) Field of Search ................................ 518/700, 713, 518/717

(56) References Cited

U.S. PATENT DOCUMENTS 2,518,583 A    8/1950   Watson

FOREIGN PATENT DOCUMENTS

| JP | 10-277382 | 10/1998 |
|----|-----------|---------|
| WO | WO 01/47802 A1 | 7/2001 |

*Primary Examiner*—J. Parsa
(74) *Attorney, Agent, or Firm*—Oblon, Spivak, McClelland, Maier & Neustadt, P.C.

(57) ABSTRACT

A reactor comprises a plurality of triple tubes having reaction tube, inner tube and central tube and disposed in a main body of the reactor, a first supply port formed in the main body and communicated with the central tube, and a second supply port formed in the main body and communicated with an annular space of triple tubes. The raw material introduced from the first supply port is fed into the catalyst layer to permit the reaction of the raw material to take place, and that as the activity of the catalyst is gradually lowered, the quantity of raw material to be fed to the first supply port is correspondingly reduced, and the quantity of raw material corresponding to this reduction of raw material is fed from the second supply port to the catalyst layer charged in the annular space.

6 Claims, 2 Drawing Sheets

METHOD OF CONDUCTING AN EXOTHERMIC REACTION

CROSS-REFERENCE TO RELATED APPLICATIONS

This application is based upon and claims the benefit of priority from the prior Japanese Patent Application No. 2001-278243, filed Sep. 13, 2001, the entire contents of which are incorporated herein by reference.

BACKGROUND OF THE INVENTION

1. Field of the Invention

This invention relates to a reacting method of raw materials, and in particular, relates to a reacting method for synthesizing a reaction product such as methanol, wherein the reaction of a raw gas such as a synthesized gas is permitted to take place in the presence of a catalyst by making use of a specific reactor.

2. Description of the Related Art

Methanol, for example, is manufactured by enabling a raw gas such as a synthesis gas comprising hydrogen, carbon monoxide and carbon dioxide to undergo the reaction thereof in a reactor filled with a catalyst. On the occasion of this manufacture of methanol, it involves an exothermic reaction.

In this reaction system involving the generation of heat, the catalyst charged inside the reactor is caused to rise in temperature, which deteriorates the activity of the catalyst. Therefore, various kinds of reactors having a specific structure for controlling the temperature rise of the catalyst-packed portion thereof have been developed.

For example, Jpn. Pat. Appln. KOKAI Publication No. 10-277382 discloses a reactor which is capable of effectively cooling the catalyst-packed portion on the occasion of the reaction of a raw gas.

According to the aforementioned publication, the reactor comprises a casing, with two tube plates for partitioning the interior of the casing into three sections, i.e. an upper chamber, a middle chamber and a lower chamber. A partitioning wall is disposed inside the upper chamber of the casing to partition the upper chamber to an unreacted gas supply chamber and an unreacted gas collecting chamber. A plurality of reaction tubes are disposed inside the casing in a manner that the upper and lower ends of each of the reaction tubes are sustained by the two tube plates. A plurality of inner tubes each having a closed lower end are disposed substantially concentrically in each of said reaction tubes. A plurality of central tubes each having an upper end secured to the partitioning wall are disposed substantially concentrically in each of the inner tubes. An annular space (catalyst-packed portion) is surrounded by and interposed between the reaction tubes and the inner tubes.

According to one embodiment (a first method) of the invention disclosed in this Jpn. Pat. Appln. KOKAI Publication No. 10-277382, methanol is synthesized by a process wherein a raw gas for example a synthesis gas comprising hydrogen, carbon monoxide and carbon dioxide is introduced from the raw gas supply chamber via the central tubs into the catalyst-packed portion to synthesize methanol. Further, according to another embodiment (a second method) thereof, methanol is synthesized by a process wherein a synthesis gas comprising hydrogen, carbon monoxide and carbon dioxide is introduced from the raw gas supply chamber via the central tubs into the catalyst-packed portion, and at the same time, another raw gas having a lower temperature than that of the first-mentioned raw gas is directly fed to the raw gas collecting chamber so as to introduce it into the catalyst-packed portion to thereby synthesize methanol.

In a reactor having a structure as mentioned above, the raw gas supply portion is formed into a triple tube structure comprising a reaction tube, an inner tube and a central tube, wherein a synthesis gas for synthesizing methanol for instance is fed via the raw gas supply chamber to the central tube. In this case, by permitting the synthesis gas to flow through the annular passageway surrounded by and formed between the central tube and the inner tube, the catalyst-packed portion charged in the annular space formed between the reaction tube and the inner tube can be cooled. As a result, it becomes possible to effectively prevent the catalyst-packed portion from rising in temperature that may be otherwise caused due to the exothermic reaction of the synthesis gas.

However, according to the first method set forth in the aforementioned publication, as the activity of the catalyst is gradually deteriorated in the latter stage of a synthesis reaction, the cooling effect of the synthesis gas flowing through the central tube of the reactor becomes somewhat excessive. As a result, the temperature of the catalyst layer becomes too low, thereby possibly deteriorating the production efficiency of methanol.

Further, according to the second method set forth in the aforementioned publication, when a catalyst exhibiting high initial activity is employed or when the flow rate of synthesis gas relative to the amount of catalyst is relatively large, for instance, the temperature of the catalyst-packed portion may exceed the permissible range at the initial stage through the middle stage of the synthesizing reaction, thereby possibly resulting in a high deterioration of the activity of the catalyst. To avoid this, it is possible to raise the ratio of synthesis gas to be fed directly to the central tube as compared with the synthesis gas to be fed to a top portion of the annular space formed between the reaction tube and the inner tube, thereby making it possible, due to the cooling effect of the synthesis gas that has been directly fed into the central tube, to control the temperature of the catalyst-packed portion to fall within the permissible range at the initial stage through the middle stage of the synthesizing reaction.

However, at the latter stage of reaction where the activity of the catalyst is caused to deteriorate, the catalyst would be excessively cooled by the synthesis gas flowing through the central tube and the inner tube of the reactor, thereby possibly deteriorating the production efficiency of methanol.

BRIEF SUMMARY OF THE INVENTION

An object of the present invention is to provide a reacting method which is featured in that the feeding system of the raw material (raw gas, for instance) to a catalyst charged in a reactor for executing the reaction of the raw gas is modified in such a manner that the temperature of the catalyst is controlled in conformity with the activity of the catalyst, thereby making it possible to execute a stable reaction of raw gas during the entire reaction period starting from the initial stage up to the latter stage thereof.

According to the present invention, there is provided a reacting method involving an exothermic reaction wherein a reaction of a raw material is executed by making use of a reactor comprising a plurality of triple tubes disposed in a main body of the reactor, each of the triple tubes comprising a reaction tube, an inner tube having a closed lower end and disposed substantially concentrically inside the reaction tube, and a central tube having an open lower end and disposed substantially concentrically inside the inner tube; a catalyst charged in an annular space formed between the inner tube and the reaction tube of the triple tubes; a first supply port formed in the main body of the reactor and communicated with the central tube; and a second supply port formed in the main body of the reactor and communicated with the annular space;

wherein the raw material introduced from the first supply port is fed via the central tube, via the space formed between the central tube and the inner tube and via an upper end of the inner tube into a layer of the catalyst to permit the reaction of the raw material to take place, and that as the activity of the catalyst is gradually lowered, the quantity of raw material to be fed to the first supply port is correspondingly reduced, and the quantity of raw material corresponding to this reduction of raw material is fed from the second supply port to the layer of the catalyst charged in the annular space.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Next, the reacting method according to the present invention will be explained with reference to drawings.

Figure 1:
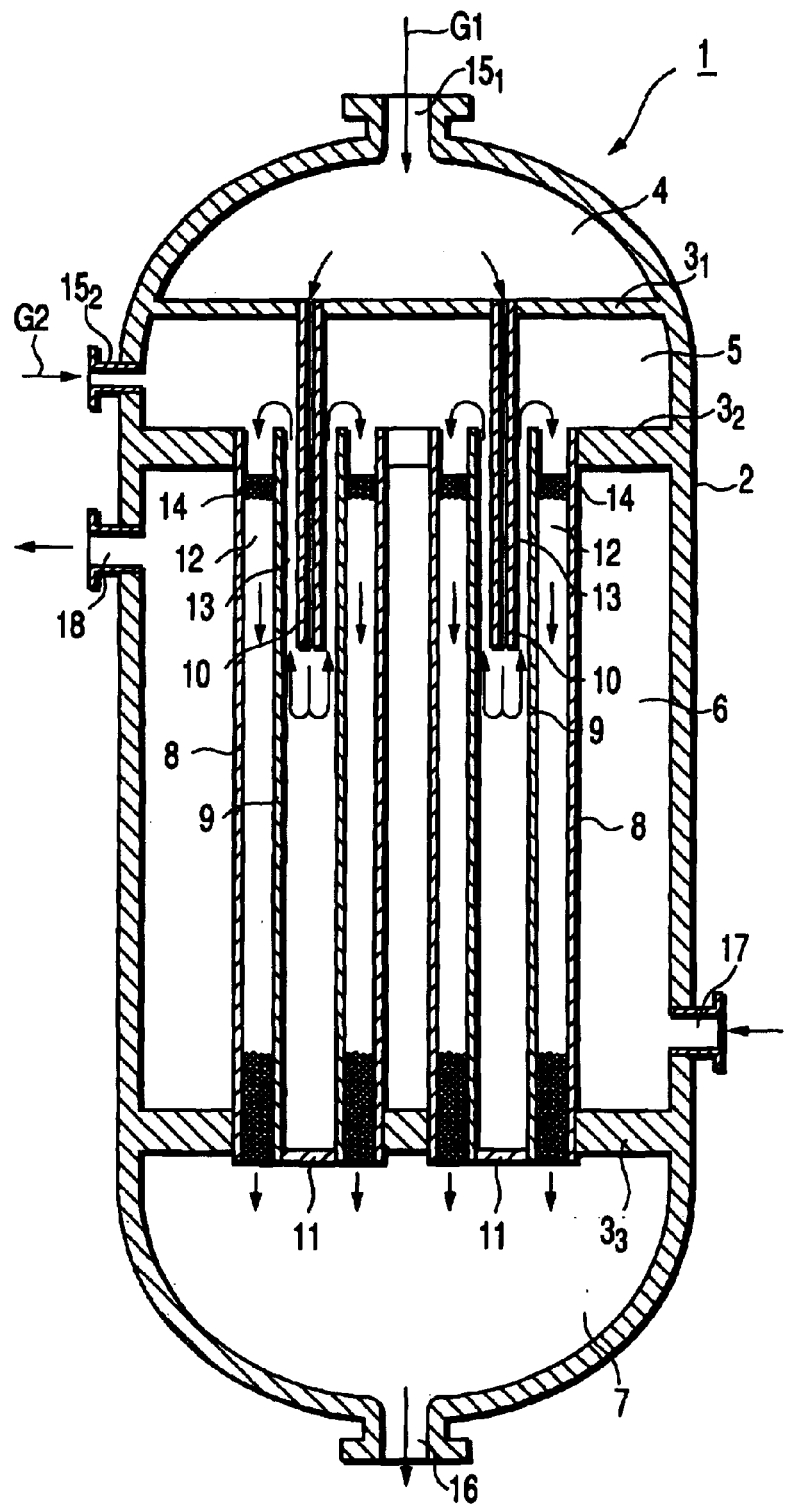
FIG. 1 is a cross-sectional view illustrating one embodiment of the reactor to be employed in a reacting method according to the present invention.
Figure 2:
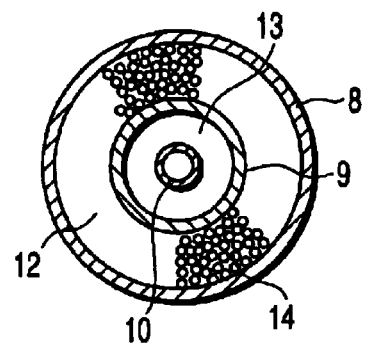
FIG. 2 is a cross-sectional view of the triple tube that can be incorporated into the reactor shown in FIG. 1.

FIG. 1 is a cross-sectional view illustrating a reactor to be employed in a reacting method according to the present invention; and FIG. 2 is a cross-sectional view of the triple tubes to be incorporated into the reactor shown in FIG. 1.

The reactor 1 is provided with a main body 2, which is partitioned by means of a first, second and third partitioning plates $3_1$, $3_2$ and $3_3$ into four chambers, i.e. from the top, a raw gas feeding chamber 4, a raw gas collecting chamber 5, a cooling medium flowing chamber 6 and a reaction product gas retention chamber 7.

As shown in FIG. 2, a reaction tube 8 and an inner tube 9 which are assembled concentric with each other are penetrated through the second and third partitioning plates $3_2$ and $3_3$ and sustained by these partitioning plates $3_2$ and $3_3$. The central tube 10 is concentrically inserted into the inner tube 9 with the upper end thereof being sustained by the first partitioning plates $3_1$.

In this triple tubes structure, the upper end of the central tube 10 is communicated with the raw gas supply chamber 4. The upper ends of the reaction tube 8 and the inner tube 9 are respectively communicated with the gas collecting chamber 5. The lower end of the inner tube 9 is closed by a shielding plate 11. The lower end of the central tube 10 is positioned close to an upper end of the inner tube 9, specifically at an upper region of the inner tube 9 which corresponds to one third of the length of the inner tube 9 as measured from the upper end thereof. Between the reaction tube 8 and the inner tube 9, there is formed an outer annular space 12. Between the inner tube 9 and the central tube 10, there is formed an inner annular space 13. A region of the outer annular space 12 is filled, from the lower end thereof up to near the upper end thereof, with a catalyst layer 14. Incidentally, a mesh plate or a porous plate (not shown) for preventing the catalyst from falling is attached to the lower end of the outer annular space 12. A plurality of the triple tubes each constructed as mentioned above are arranged inside the main body 2 of the reaction tube 2.

A first supply port $15_1$ is provided at an upper portion of the main body 2 so as to communicate with the raw gas supply chamber 4. The second supply port $15_2$ is provided at an upper sidewall of the main body 2 so as to communicate with the raw gas collecting chamber 5. An exhaust port 16 for discharging a product gas is provided at a lower end of the main body 2 of the reactor 1. An inlet port 17 for the cooling medium is provided at a lower sidewall portion of the main body 2 of the reactor 1 where the cooling medium flowing chamber 6 is located. An outlet port 18 for the cooling medium is provided at an upper sidewall portion of the main body 2 of the reactor 1 where the cooling medium flowing chamber 6 is located.

Next, a reacting method of the present invention will be explained with reference to the reactor shown in FIGS. 1 and 2.

First of all, a raw gas G1 is fed from the first supply port $15_1$ shown in FIG. 1 to the raw gas supply chamber 4 in the main body 2 of the reactor. The raw gas G1 existing inside the raw gas supply chamber 4 is permitted to enter into the central tube 10 of the triple tubes from the opening formed at the upper end of the central tube 10 and to flow downward through the central tube 10, thus enabling the raw gas G1 to enter from the outlet port formed at the lower end of the central tube 10 into the inner annular space 13 formed between the central tube and the inner tube 9. The raw gas G1 is further permitted to flow upward through the inner annular space 13 and to flow from the upper end of the outer annular space 12 formed between the inner tube 9 and the reaction tube 8 into the catalyst layer 14 filled in this outer annular space 12. While the raw gas G1 passes through the catalyst layer 14, the raw gas G1 is allowed to take place the reaction thereof to produce a desired reaction product gas. Specifically, this raw gas is subjected to an exothermal reaction involving the generation of heat in the presence of the catalyst, thereby manufacturing the reaction product gas. This reaction product gas is then transferred via the lower end of the outer annular space 12 to a reaction product gas retention chamber 7 from which it is finally discharged through the exhaust port 16.

In this manufacture of the reaction product gas, a cooling medium is supplied from the cooling medium inlet port 17 to the cooling medium flowing chamber 6 of the main body 2 of the reactor 1 and then discharged from the cooling medium outlet port 18, thereby cooling the catalyst layer 14 through the cooling of the reaction tube 8 of the triple tube. Further, since the raw gas G1 is permitted to pass through the central tube 10 and the inner annular space 13, and then to pass through the upper end of the outer annular space 12 filled with the catalyst layer 14, the catalyst layer 14 is cooled also from the inner side thereof by the raw gas G1. Namely, since the region of the catalyst layer 14 where temperature is caused to rise prominently due to the exothermic reaction in the manufacturing process of the reaction product gas is cooled by the cooling medium and the raw gas G1 as mentioned above, any excessive rise in temperature of the catalyst layer due to the exothermic reaction can be effectively suppressed.

In the process of manufacturing the reaction product gas by the feeding of raw gas G1 to the catalyst layer 14 as mentioned above, the activity of the catalyst which is located in the vicinity of the upper portion of the outer annular space 12 is caused to deteriorate. On this occasion, the supply flow rate F1 of the raw gas G1 to the first supply port $15_1$ is gradually decreased, and the raw gas G2 is fed via the second supply port $15_2$ to the raw gas collecting chamber 5 at a flow rate F2 corresponding to the magnitude of decrease in flow rate of raw gas G1. In this case, "the flow rate" of the raw gas G2 corresponding to the magnitude of decrease in flow rate of raw gas G1 is generally approximately the same as the magnitude of decrease in flow rate of the raw gas G1. However, depending on the degree of degradation of the catalyst and on the reaction efficiency desired, the flow rate of the raw gas G2 corresponding to the magnitude of decrease in flow rate of raw gas G1 may be increased or decreased relative to the magnitude of decrease in flow rate of raw gas G1.

In the supply system of raw gas from such two flow lines, the raw gas G1 is permitted to enter into the catalyst layer 14 charged inside the outer annular space 12 from the upper end of the outer annular space 12 after passing through the central tube 10 and the inner annular space 13. On the other hand, the raw gas G2 is permitted to enter into the catalyst layer 14 charged inside the outer annular space 12 from the upper end of the outer annular space 12 after being combined with the raw gas G1. While this combined raw gas passes through the catalyst layer 14, the combined raw gas is allowed to take place the reaction thereof to produce a desired reaction product gas. This reaction product gas is then transferred via the lower end of the outer annular space 12 to a reaction product gas retention chamber 7 from which it is finally discharged through the exhaust port 16.

As for the kind of raw gas useful in this case, it is possible to employ a synthesis gas comprising hydrogen, carbon monoxide and carbon dioxide, which is generally employed in the synthesis of methanol for instance.

As for the catalyst, more specifically, the catalyst which can be employed for the synthesis of methanol for instance, it is possible to employ a copper-based catalyst. In particular, it is preferable to employ a catalyst made of an oxide which is excellent in durability in an atmosphere containing a high concentration of carbon dioxide, the oxide comprising Cu, Zn, Al, Ga and M (at least one element selected from alkaline earth metal elements and rare earth elements) and having a composition wherein Cu, Zn, Al, Ga and M are mixed together at atomic ratios of: Cu:Zn:Al:Ga:M=100:10–200:1–20:1–20:0.1–20.

The timing of feeding the raw gas G2 to the raw gas collecting chamber 5 should preferably be performed after an elapse of time which corresponds to 30 as the servicing period of the catalyst layer which has been charged in the outer annular space of the triple tube is assumed as being 100. It is preferable in this case that the supply flow rate of the raw gas G2 is increased gradually or stepwise.

According to the present invention as described above, the temperature of the catalyst filled in the annular space formed between the inner tube and the reaction tube of the triple tubes structure is controlled in conformity with the degree of activity of the catalyst, thereby making it possible to perform a stabilized reaction of raw gas during the entire reaction period, i.e. from the initial stage up to the last stage of the reaction.

Namely, when the reaction (exothermic reaction) of the raw gas is permitted to take place in the presence of a catalyst which has been filled in an annular space formed between the reaction tube and the inner tube in the reactor of triple tubes structure explained above, the following conditions are required and at the same time, specific features would be appeared.

1) If the reactivity of the raw gas is to be retained, the catalyst is required to be maintained in a suitable temperature range.

2) Any excessive temperature rise of the catalyst layer may lead to deterioration in the activity of the catalyst itself.

3) Deterioration in the activity of the catalyst is related, as a trade-off, with the heat release value on the occasion of the reaction of raw gas. More specifically, in a reaction wherein the raw gas is fed from the upper side of the catalyst layer placed in the annular space of the triple tubes, if the activity of the catalyst existing at the upper portion of the catalyst layer is relatively high, the heat value to be released from the reaction of the raw gas becomes larger. On the other hand, when the activity of the catalyst is decreased, the heat to be released from the reaction of the raw gas becomes less. In particular, a portion of the catalyst layer which is disposed at a region extending from the top to the middle portion of the annular space is readily heated up to a high temperature in the initial stage of the operation of the device, thus deteriorating the activity of that portion of the catalyst and therefore, the heat release value is lowered.

Incidentally, when the raw gas is fed only through the first supply port to the catalyst layer placed in the annular space of the triple tube after the raw gas being permitted to pass through the central tube of the reactor of triple tube structure and through the space formed between this central tube and the inner tube, a portion of the catalyst layer which is disposed at a region extending from the top to the middle portion of the annular space is deteriorated in activity thereof and therefore, the heat release value is lowered. Accordingly, in the latter stage of the reaction, the catalyst layer is excessively cooled as the raw gas permitted to pass through the space formed between the central tube and the inner tube. As a result, the temperature of the catalyst layer becomes lower than the temperature which is optimal for the reaction of the raw gas, thus deteriorating the reaction efficiency of the raw gas.

Whereas, according to the present invention, when the catalyst, in particular, a portion of the catalyst layer which is disposed at a region extending from the top to the middle portion of the annular space is deteriorated in activity thereof, the supply flow rate F1 of the raw gas G1 to the inner tube of the triple tube through the first supply port is gradually decreased, and at the same time, the raw gas G2 is fed from the second supply port directly to the upper end of the annular space formed between the inner tube of the triple tubes and the reaction tube at a flow rate F2 corresponding to the magnitude of decrease in flow rate of raw gas G1. With of this method, the degree of cooling of the triple tubes structure can be suitably controlled during the process where the raw gas G1 is permitted to pass from the central tube to the upper end of the annular space, thereby making it possible to prevent an excessive cooling of the catalyst layer that has been decreased in heat release value due to the lowering of the activity thereof. As a result, since the reactions of the raw gases G1 and G2 are allowed to take place at the catalyst layer which is kept at an optimal temperature, it becomes possible to maintain almost the same degree of reaction efficiency as that of the initial stage of reaction even in the latter stage of the reaction where the catalyst is caused to deteriorate in activity.

Further, when the raw gas G1 is fed from the first supply port via the central tube and the space formed between this central tube and the inner tube to the catalyst layer placed in the annular space formed between the inner tube and the reaction tube, the pressure loss of the raw gas G1 is increased as compared with the case where a raw gas is directly fed to the upper end of the annular space.

Whereas, according to the present invention, when the activity of catalyst is deteriorated, the supply flow rate of the raw gas G1 to the passageway where the aforementioned pressure loss is brought about is decreased, and instead, the raw gas G2 is fed directly to the upper end of the annular space at a flow rate corresponding to the magnitude of decrease in flow rate of raw gas G1. As a result, the total pressure loss on the occasion of feeding the raw gas can be minimized.

Incidentally, although a raw gas is employed as a raw material in the foregoing embodiment, it is possible to employ, as a raw material, other kinds of fluid other than gas.

EXAMPLE 1

Figure 3:
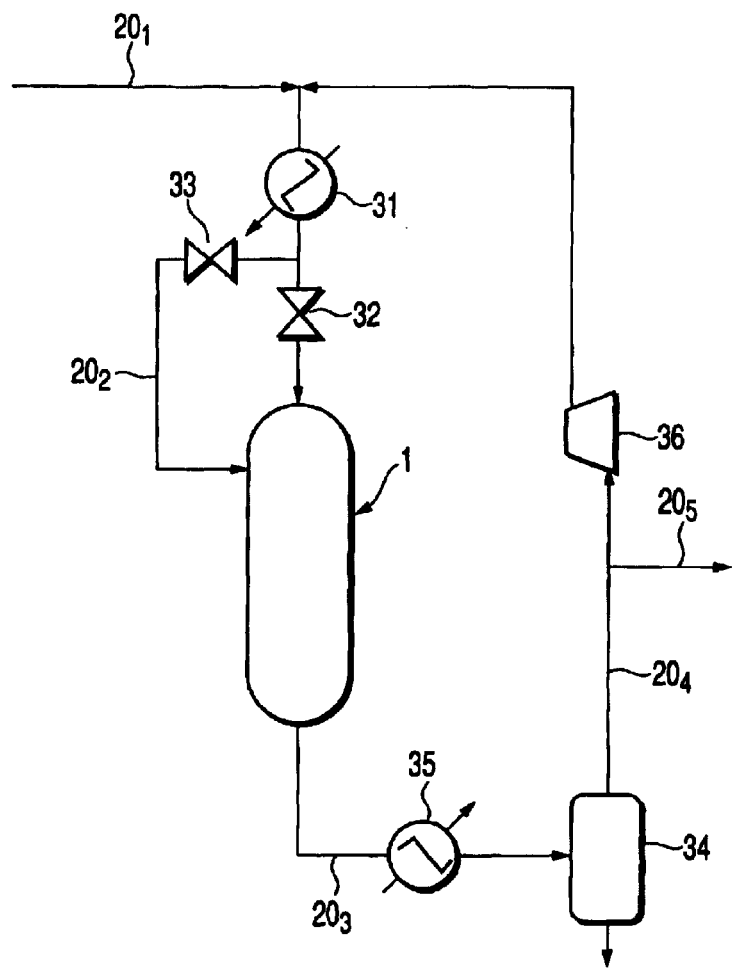
FIG. 3 is a diagram schematically illustrating a main portion of a methanol-manufacturing plant into which the reactor shown in FIG. 1 is incorporated.

FIG. 3 shows a main portion of a methanol manufacturing plant, into which the reactor shown in FIGS. 1 and 2 is incorporated.

The reactor 1 is connected through the first supply port 15₁ with a passageway 20₁. A high-pressure synthesis gas (raw gas) comprising as main components hydrogen, carbon monoxide and carbon dioxide and synthesized at the reformer is permitted to pass through the passageway 20₁. This passageway 20₁ is provided with a preheater 31 for preheating the synthesis gas. In addition, this passageway 20₁ is branched at a portion thereof which is located between the preheater 31 and the reactor 1, thereby providing a branched passageway 20₂ which is connected with the second supply port 15₂ of the reactor 1. Both passageway 20₁ and branched passageway 20₂ are provided with adjustable valves 32 and 33, respectively.

The exhaust port 16 of the reactor 1 is connected, via a passageway 20₃, with a gas-liquid separator 34. This passageway 20₃ is provided with a cooler 35. The gas-liquid separator 34 is connected via a gas-circulating passageway 20₄ with the passageway 20₁. This gas-circulating passageway 20₄ is provided with a gas compressor 36. A purge gas passageway 20₅ is branched from a region of the gas-circulating passageway 20₄ which is located between the gas-liquid separator 34 and the gas compressor 36.

Incidentally, the catalyst charged in the outer annular space 12 formed between the inner tube 9 and the reactor 8 of the triple tube of the reactor 1 is formed of a composition wherein Cu, Zn, Al, Ga and M are mixed together at atomic ratios of: Cu:Zn:Al:Ga:M=100:10–200:1–20:1–20:0.1–20.

Next, the method of manufacturing methanol will be explained with reference to the aforementioned methanol manufacturing plant.

First of all, the valve 32 attached to the passageway 20₁ was opened, and the valve 33 attached to the branched passageway 20₂ was closed. Then, a high-pressure synthesis gas (50–150 atm, for example) was fed from the first supply port 15₁ via the passageway 20₁ to the raw gas supply chamber 4 of the main body 2 of reactor. On this occasion, the high-pressure synthesis gas was heated by the preheater 31 mounted on the passageway 20₁ up to a temperature (for example, 160–240° C.) which is suited for the methanol synthesis reaction. By the way, the unreacted gas, which had been separated at the gas-liquid separator 34, was fed through the gas circulating passageway 20₄ to a region of the passageway 20₁ which was located immediately before the preheater 31, thereby enabling the unreacted gas to be mixed with the synthesis gas.

The raw gas (synthesis gas) G1 that had been introduced into the raw gas supply chamber 4 of the reactor 1 was permitted to inter into the central tube 10 of triple tubes structure from the inlet port provided at the upper end thereof and to flow downward from the top to bottom of the central tube 10. Then, the raw gas was discharged from the outlet port provided at the bottom of the central tube 10 and introduced into the inner annular space 13 formed between the central tube 10 and the inner tube 9. The synthesis gas G1 was further permitted to flow upward while passing through the inner annular space 13 and to enter from the upper end of the outer annular space 12 formed between the inner tube 9 and the reaction tube 8 into the catalyst layer 14 placed inside the outer annular space 12. Where the synthesis gas G1 was permitted to pass through the catalyst layer 14, the reactions as shown in the following formulas (1) and (2) took place to synthesize methanol.

$$CO + 2H_2 \leftrightarrows CH_3OH \tag{1}$$

$$CO_2 + 3H_2 \leftrightarrows CH_3OH + H_2O \tag{2}$$

During this synthesis of methanol, a cooling medium such as boiler water was fed from the cooling medium inlet port 17 to the cooling medium flowing chamber 6 of the main body 2 of the reactor 1 and was discharged from the cooling medium outlet port 18, thereby cooling the catalyst layer 14 through the cooling of the reaction tube 8. Further, the reaction region where the methanol synthesis reaction was involved was formed into a triple tubes structure, and additionally, the synthesis gas was permitted to pass through the central tube 10 and the inner annular space 13, and then to pass through the upper end of the outer annular space 12 filled with the catalyst layer 14. Therefore, the catalyst layer 14 was allowed to cool from the inner side thereof by this synthesis gas. Namely, as described above, it was possible, by means of the cooling medium and the synthesis gas, to cool the region of the catalyst layer 14 which was disposed close to the synthesis gas inlet port where the temperature rise was most prominent due to the exothermic reaction in the synthesizing process of methanol.

The product gas containing the methanol thus obtained was then permitted to flow to the passageway 20₃ from the exhaust port 16 of the reaction product gas retention chamber 7 of the main body 2 of reactor 1 and to enter into the cooler 35. Most of methanol and water in the product gas that had been cooled in the cooler 35 was allowed to condense and was transferred in a liquid state to the gas-liquid separator 34. In this gas-liquid separator 34, liquid crude methanol was separated from unreacted gas.

The feeding of the raw gas G1 to the catalyst layer 14 from the first supply port 15₁ was performed at a flow rate F1 throughout a period of 0 to 30 (initial period) as the servicing period of the catalyst layer was assumed as being 100. Thereafter, the opening degree of both valves 32 and 33 mounted respectively on the passageway 20₁ and the branched passageway 20₂ was adjusted to thereby allow not only the synthesis gas G1 but also the raw gas (synthesis gas) G2 to be introduced via the second supply port 15₂ into the raw gas collecting chamber 5 while controlling the flow rate of these synthesis gases. Namely, in this synthesis of methanol, these synthesis gases G1 and G2 were introduced into the catalyst layer 14 in such a manner that the flow rates F1 and F2 of these synthesis gases G1 and G2 could be controlled to F1/F2=80/20 throughout a period of 30 to 60

(intermediate period) as the servicing period of the catalyst layer was assumed as being 100.

Thereafter, the opening degree of both valves 32 and 33 mounted respectively on the passageway $20_1$ and the branched passageway $20_2$ was adjusted so as to enable these synthesis gases G1 and G2 to be introduced into the catalyst layer 14 in such a manner that the flow rates F1 and F2 of these synthesis gases G1 and G2 could be controlled to F1/F2=63/37 throughout a period of 60 to 100 (latter period) as the servicing period of the catalyst layer was assumed as being 100, thereby synthesizing methanol.

COMPARATIVE EXAMPLE 1

By making use of the aforementioned methanol manufacturing plant shown in FIG. 3, into which the reactor shown in FIGS. 1 and 2 was incorporated, methanol was synthesized in the same manner as described in Example 1 except that the raw gas (synthesis gas) G1 was introduced into the catalyst layer 14 from the first supply port $15_1$ at a flow rate F1 throughout the entire operating period as the servicing period of the catalyst layer was assumed as being 100.

COMPARATIVE EXAMPLE 2

By making use of the aforementioned methanol manufacturing plant shown in FIG. 3, into which the reactor shown in FIGS. 1 and 2 was incorporated, methanol was synthesized in the same manner as described in Example 1 except that the opening degree of both valves 32 and 33 mounted respectively on the passageway $20_1$ and the branched passageway $20_2$ was adjusted to thereby introduce the synthesis gases G1 and G2 into the catalyst layer 14 in such a manner that the flow rates F1 and F2 of these synthesis gases G1 and G2 could be controlled to F1/F2= 63/37 throughout the entire operating period as the servicing period of the catalyst layer was assumed as being 100.

Then, in the synthesizing operations of methanol in Example 1 and Comparative Examples 1 and 2, the pressure loss of the reactor and the throughput of methanol were investigated throughout the entire operating period, i.e. from the initial stage to the latter stage of reaction, the results being shown in the following Table 1. Incidentally, the pressure loss of the reactor and the throughput of methanol were determined based on the reference value (100) which was obtained in the initial stage of reaction in Comparative Example 1, hence all the values shown therein being indicated as relative values based on this reference value.

TABLE 1

| | | Operating period | | |
|---|---|---|---|---|
| | | 0–30 (Initial stage) | 30–60 (Intermediate stage) | 60–100 (Latter stage) |
| Comparative Example 1 | F1/F2 ratio | 100/0 | 100/0 | 100/0 |
| | Pressure loss in reactor | 100 | 100 | 100 |
| | Throughput of methanol | 100 | 99 | 99 |
| Comparative Example 2 | F1/F2 ratio | 63/37 | 63/37 | 63/37 |
| | Pressure loss in reactor | 95 | 95 | 95 |
| | Throughput of methanol | —* | —* | 100 |
| Example 1 | F1/F2 ratio | 100/0 | 80/20 | 63/37 |
| | Pressure loss in reactor | 100 | 97 | 95 |
| | Throughput of methanol | 100 | 100 | 100 |

*The maximum temperature of the catalyst layer exceeded the allowable temperature.

As clearly seen from Table 1, in the case of Comparative Example 1 wherein only the synthesis gas G1 was supplied to the reactor throughout the entire operating period, i.e. from the initial stage to the latter stage of reaction, the throughput of methanol was decreased at the latter stage of operation where the activity of the catalyst was deteriorated. This can be attributed to the fact that since the cooling effect of the central tube of the triple tubes structure became excessive at the latter stage of operation where the activity of the catalyst was deteriorated, the temperature of the catalyst layer became too low.

On the other hand, in the case of Comparative Example 2 wherein the flow rates F1 and F2 of synthesis gases G1 and G2 were constantly set to F1/F2=63/37 throughout the entire operating period, i.e. from the initial stage to the latter stage of reaction, the temperature of the catalyst exceeded the allowable range in a period beginning from the initial stage up to the intermediate stage of operation, thereby badly deteriorating the activity of the catalyst, thus making it unpractical.

Whereas, in the case of Example 1 wherein the ratio of the flow rates F1 and F2 of synthesis gases G1 and G2 were altered during the operating period, i.e. from the initial stage to the latter stage thereof, it was possible to maintain the throughput of methanol at the same level as that of the initial stage of operation of Comparative Example 1 and at the same time, to minimize the pressure loss of the reactor during the operating period starting from the initial stage up to the latter stage thereof.

As described above, according to the present invention, it is possible to provide a reacting method which is featured in that the feeding system of raw gas to a catalyst charged in a reactor for executing the reaction of the raw gas is modified in such a manner that the temperature of the catalyst is controlled in conformity with the activity of the catalyst, thereby making it possible to execute a stable reaction of raw gas beginning from the initial stage up to the latter stage of the reaction. Therefore, the reacting method according to the present invention is advantageous in the synthesis of methanol, etc.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of performing an exothermic reaction, comprising:

introducing a raw material through a first supply port in the raw gas chamber of a reactor comprising a plurality of triple tubes disposed in the main body of the reactor, each of said triple tubes comprising a reaction tube, an inner tube having a closed lower end and disposed substantially concentrically inside the reaction tube, and a central tube having an open lower end and disposed substantially concentrically inside the inner tube; a catalyst charged in the annular space formed between the inner tube and the reaction tube of each triple tube; a first supply port formed in the main body of the reactor and in communication with each central tube; and a second supply port formed in the main body of the reactor and in communication with the annular space of each triple tube, whereby the raw material flows through each central tube of each triple tube and then continues to flow into and through said space formed between the central tube within the inner tube and then into the upper end of the inner tube and through the annular space charged with catalyst thereby effecting said exothermic reaction; and as the activity of the catalyst decreases, decreasing the supply of raw material introduced into the reactor through the first supply port and at the same time introducing raw material into said second supply port that communicates with the catalyst in each annular space in an amount that corresponds to the reduced amount of gas that would have been introduced into said first supply port.

2. The method according to claim 1, wherein said raw material is a raw gas.

3. The method according to claim 2, wherein said raw gas is a synthesis gas comprising hydrogen, carbon monoxide and carbon dioxide, and said catalyst is a methanol synthesizing catalyst.

4. The method according to claim 3, wherein said methanol synthesizing catalyst is formed of an oxide comprising Cu, Zn, At, Ga and M, wherein M is at least one element selected from the group consisting of the alkaline earth metals elements and rare earth elements, oxide having a composition wherein the Cu, Zn, Al, Ga and M are mixed together at in atomic ratios of: Cu: Zn: Al: Ga: M=100:10–200:1–20:1–20:0.1–20.

5. The method according to claim 2, wherein said raw gas is fed from the second supply port after an elapse of time which corresponds to 30 on the basis of the servicing period of the catalyst layer which has been charged in the annular spaces of the triple tubes being set to 100.

6. The reacting method according to claim 5, wherein said raw gas to be fed from the second supply port is increased in quantity in steps.

* * * * *